United States Patent
Wang et al.

(10) Patent No.: US 10,209,197 B2
(45) Date of Patent: Feb. 19, 2019

(54) METHOD FOR INSPECTING AGING STATE OF SILICONE RUBBER COMPOSITE INSULATING MATERIAL

(71) Applicant: Graduate School at Shenzhen, Tsinghua University, Shenzhen, Guangdong (CN)

(72) Inventors: Xilin Wang, Guangdong (CN); Han Wang, Guangdong (CN); Weian Ye, Guangdong (CN); Zhidong Jia, Guangdong (CN)

(73) Assignee: GRADUATE SCHOOL AT SHENZHEN, TSINGHUA UNIVERSITY, Shenzhen, Guangdong (CN)

( * ) Notice: Subject to any disclaimer, the term of this patent is extended or adjusted under 35 U.S.C. 154(b) by 0 days.

(21) Appl. No.: 15/836,323

(22) Filed: Dec. 8, 2017

(65) Prior Publication Data
US 2018/0100804 A1 Apr. 12, 2018

Related U.S. Application Data

(63) Continuation of application No. PCT/CN2016/072533, filed on Jan. 28, 2016.

(30) Foreign Application Priority Data

Jan. 15, 2016 (CN) .......................... 2016 1 0029402

(51) Int. Cl.
  *G01J 3/30* (2006.01)
  *G01N 21/71* (2006.01)
  (Continued)

(52) U.S. Cl.
  CPC ............ *G01N 21/718* (2013.01); *G01J 3/443* (2013.01); *G01N 21/952* (2013.01); *H01B 3/28* (2013.01); *H01B 3/46* (2013.01)

(58) Field of Classification Search
  CPC ...... G01N 21/62; G01N 21/63; G01N 21/718; G01N 21/952; G01N 2001/045; G01J 3/443; H01B 3/28; H01B 3/46
  (Continued)

(56) References Cited

U.S. PATENT DOCUMENTS

| | | | | |
|---|---|---|---|---|
| 5,537,207 | A | * | 7/1996 | Carlhoff ............... G01N 21/718 356/317 |
| 5,751,416 | A | * | 5/1998 | Singh ........................ G01J 3/30 356/300 |
| 2014/0085631 | A1 | * | 3/2014 | Lacour .................. G01J 3/0208 356/316 |

FOREIGN PATENT DOCUMENTS

| CN | 102519918 A | 6/2012 |
|---|---|---|
| CN | 102749316 A | 10/2012 |

(Continued)

OTHER PUBLICATIONS

In et al, Rapid quantitative analysis of elemental composition and depth profile of Cu(In,Ga)Se2 thin solar cell film using laser-induced breakdown spectroscopy, Thin Solid Films vol. 579, Mar. 31, 2015, pp. 89-94.*

(Continued)

*Primary Examiner* — Tarifur R Chowdhury
*Assistant Examiner* — Jonathon Cook
(74) *Attorney, Agent, or Firm* — Hamre, Schumann, Mueller and Larson, P.C.

(57) ABSTRACT

A method for inspecting an aging state of a silicone rubber composite insulating material comprises the following steps: bombarding, for multiple times and by a pulsed laser beam, selected points on a surface of a silicone rubber composite insulating material to be inspected to generate a plasma; collecting spectrum information emitted by the plasma at each bombardment, and extracting, from the collected spectrum information, a spectral property indicator of a specific (Continued)

constituent element of the silicone rubber composite insulating material at each bombardment; and determining aging state information of the silicone rubber composite insulating material according to the change pattern of the spectral property indicator of the specific constituent element with respect to the bombardment depth. The method enables the rapid and accurate inspection of an aging state of a silicone rubber composite insulating material, and avoids the destructive tests required in the prior art.

10 Claims, 1 Drawing Sheet

(51) Int. Cl.
*G01J 3/443* (2006.01)
*G01N 21/952* (2006.01)
*H01B 3/28* (2006.01)
*H01B 3/46* (2006.01)

(58) Field of Classification Search
USPC ............................................. 356/318
See application file for complete search history.

(56) References Cited

FOREIGN PATENT DOCUMENTS

| CN | 103018215 A | 4/2013 |
|---|---|---|
| CN | 103018216 A | 4/2013 |
| CN | 103234943 A | 8/2013 |
| CN | 103424397 A | 12/2013 |
| CN | 104345025 A | 2/2015 |
| CN | 104764708 A | 7/2015 |
| JP | H05259250 A | 10/1993 |
| JP | H09281044 A | 10/1997 |
| JP | 3816838 B2 | 8/2006 |

OTHER PUBLICATIONS

Kokkinaki et al, Assessing the Type and Operational Quality of SIR HV Insulators by Remote Libs Analysis, Conference: 8th Euro-Mediterranean Symposium on Laser Induced Breakdown Spectroscopy, Johannes Kepler University Linz, Austria, Sep. 14-18, 2015, At Johannes Kepler University Linz, Austria.*

Rezaei et al, Assessment of in Service Composite Insulators in Very Harsh Coastal Environment of Iran: Laboratory & Field Testing, 21st International Conference on Electricity Distribution Frankfurt, Jun. 6-9, 2011, Paper 1266.*

Qu et al.; "Judge of surface scratch defects on automobile steel sheets by laser induced breakdown spectrometry", with English translation of the abstract; Metallurgical Analysis, Feb. 15, 2013, vol. 2, pp. 13-17, 5 pages.

Sun et al., "Simultaneous Quantitative Analysis of Multielements in AL Alloy Samples by Laser Induced Breakdown Spectroscopy", with English translation of the abstract; Spectroscopy and Spectral Analysis, Dec. 15, 2009, vol. 29, No. 12, pp. 3375-3378, 4 pages.

Li et al., "Depth distribution analysis of copper in copper infiltration zone of welding joint surface by laser induced breakdown spectrometry", with English translation of the abstract; Metallurgical Analysis, Feb. 3, 2015, vol. 1, pp. 19-25, 7 pages.

International Search Report (English and Chinese) and Written Opinion of International Application No. PCT/CN2016/072533 dated Oct. 31, 2016, 9 pages.

* cited by examiner

METHOD FOR INSPECTING AGING STATE OF SILICONE RUBBER COMPOSITE INSULATING MATERIAL

CROSS REFERENCE TO RELATED APPLICATIONS

This application is a continuation application of PCT/CN2016/072533, filed on Jan. 28, 2016, which claims the priority of China patent application No. 201610029402.3 filed on Jan. 15, 2016. The contents of the above-mentioned applications are all hereby incorporated by reference.

BACKGROUND

Field of the Invention

The present invention relates to a method for inspecting an aging state of a silicone rubber composite insulating material.

Related Arts

Good external insulation status of a power transmission line is an important guarantee for the safe operation of a power system. The anti-fouling performance of externally insulating equipment is greatly improved only after silicone rubber materials represented by composite insulators (synthetic insulators), sheds and silicone rubber coating (RTV coating) vulcanized at room temperature are widely used in the external insulation area of the power system.

During the long-term operation of the composite materials, aging occurs due to the influence from the electric field, temperature, humidity and other factors, resulting in the degradation of the composite material and thus threatening the safe and stable operation of the power transmission line. Therefore, it is of great significance to determine the aging status of a composite material on a power transmission line.

Silicone rubber materials are commonly used composite insulating materials in the power system, and are widely used in the field of high-voltage external insulation. After long-term operation, aging of the silicone rubber materials occurs, causing the degradation of the materials. In order to ensure reliable external insulation of a power transmission line, the aging state of the composite insulating material on a power transmission line needs to be determined.

At present, methods for determining the aging state of composite insulating materials include Fourier transform infrared spectroscopy (FTIR), chemical analysis methods such as thermogravimetry (TG), hydrophobicity testing, and vibrational and acoustic testing. However, the aging state is difficult to be determined by the hydrophobicity testing effectively; in the chemical analysis method, destructive tests are needed to obtain a sample and the method cannot be carried out on-site; and the vibrational and acoustic testing is only applicable to the case in which the composite material is aged and has large defects.

In general, the aging of material is a process gradually occurring from the surface to the interior. The chemical composition and various physical properties of the material also change from the inside to the outside as the aging occurs. The internal and surface states of a material can be characterized to a certain degree by a slicing method. However, this method is very rough and it is difficult to obtain the detailed process information of the change in the material composition along the Z-axis (depth direction). Therefore, there is an urgent need at present for a method for characterizing and investigating a change pattern (in the composition or performance) of a composite material from the surface to the interior.

SUMMARY

In view of the disadvantages existing in the prior art, the present invention mainly aims at providing a method for inspecting an aging state of a silicone rubber composite insulating material, so as to enable the rapid and accurate inspection of an aging state of a composite material, and avoids the destructive tests required in the prior art.

To achieve the above object, the following technical solution is adopted in the present invention.

A method for inspecting an aging state of a silicone rubber composite insulating material comprises the following steps:

S1: bombarding, for multiple times and by a pulsed laser beam, selected points on a surface of a silicone rubber composite insulating material to be inspected to generate a plasma, and measuring a bombardment depth formed in the silicone rubber composite insulating material after each bombardment;

S2: collecting spectrum information emitted by the plasma at each bombardment, and extracting, from the collected spectrum information, a spectral property indicator of a specific constituent element of the silicone rubber composite insulating material at each bombardment, wherein the spectral property indicator comprises at least a spectral-line intensity characteristic of a characteristic spectral line;

S3: determining a change pattern of the spectral property indicator of the specific constituent element with respect to the bombardment depth; and S4: determining aging state information of the silicone rubber composite insulating material according to the change pattern of the spectral property indicator of the specific constituent element with respect to the bombardment depth, wherein the aging state information comprises at least aging depth information of the silicone rubber composite insulating material.

Further, the selected points comprise a plurality of selected points at different locations on the surface of the silicone rubber composite insulating material; and in Step S4, average aging state information of the silicone rubber composite insulating material at the plurality of selected points is determined.

Further, in Step S1, the selected points on the surface of the silicone rubber composite insulating material to be inspected are bombarded for multiple times by a pulsed laser beam under the same bombardment conditions. In Step S3, a change pattern of the spectral property indicator of the specific constituent element with respect to the number of bombardments is determined, to reflect the change pattern of the spectral property indicator of the specific constituent element with respect to the bombardment depth. In Step S4, the aging depth information of the silicone rubber composite insulating material is determined according to a linear relationship between the bombardment depth and the number of bombardments under the same bombardment conditions and the change pattern of the spectral property indicator of the specific constituent element with respect to the number of bombardments.

Further, the bombardment conditions comprise single pulse energy, frequency, spot area, and angle of bombardment of the pulsed laser beam.

Further, in Step S2, the specific constituent element detected comprises a first element and a second element, characteristic spectral lines of the first element and the second element at each bombardment are determined from the collected spectrum information, and a spectral line intensity ratio of the second element to the first element is calculated. In Step S3, a change pattern of the spectral line intensity ratio of the second element to the first element with respect to the bombardment depth is determined. In Step S4, the aging state information of the silicone rubber composite insulating material is determined according to the change pattern of the spectral line intensity ratio of the second element to the first element with respect to the bombardment depth.

Further, in Step S2, an element with a relatively stable spectral line intensity at the multiple bombardments is selected as the first element, and an element with a relatively unstable spectral line intensity at the multiple bombardments is selected as the second element.

Further, the spectral property indicator further comprises the temperature and the electron density of the plasma.

Further, the silicone rubber composite insulating material is a composite material for power transmission lines and transformer equipment.

Further, the composite material for power transmission lines comprises a variety of externally insulating composite materials, for example, an RTV coating of an insulator, a shed material of a composite insulator, or a transformer sheathing material.

Further, the inspection is carried out with an LIBS system.

The present invention has the following beneficial effects.

Considering the fact that destructive tests (for example, peeling a RTV coating off from an insulator, or cutting a composite insulator shed off from a plug) are required in an existing method for determining the aging state of a silicone rubber composite material, and other acoustic and optical test methods are merely applicable to composite materials having large defects (cracks or holes), the present invention provides a method for inspecting an aging state of a silicone rubber composite insulating material, in which the aging state of a composite insulating material on a power transmission line is rapidly and reliably inspected by establishing a change pattern of a characteristic spectral line strength of an element with respect to the depth in the silicone rubber composite insulating material by bombarding the surface of the composite insulating material using a pulsed laser beam. In the method for inspecting an aging state of a silicone rubber composite insulating material according to the present invention, the aging state of a silicone rubber composite insulating material can be determined quickly by a laser induced breakdown spectroscopy system, and the method can be used on-site.

Specifically, the laser from a pulsed laser source is focused on the surface of an RTV silicone rubber material of an insulator or the surface of a composite insulator to be inspected, and partially vaporizes the surface of the to-be-inspected silicone rubber composite insulating material to form a plasma. The spectrum information emitted during the plasma expansion and cooling process is collected. The composition of the silicone rubber composite insulating material, the characteristic spectral line intensity of a specific constituent element, the spectral line intensity ratio, the temperature and the electron density of the plasma and other spectral property indicators are extracted from the collected emission spectrum of the plasma. The aging state of the silicone rubber composite insulating material can be determined quickly by making use of the correlation between these indicators and the aging state of the silicone rubber composite insulating material.

In the present invention, on the basis of macro inspection, an LIBS device is employed to inspect the composite material to be tested (RTV coating or a shed material of a composite insulator) by making use of the characteristics that the laser-induced plasma spectrum is extremely sensitive to the characteristic change of an object to be tested and has high spatial resolution, so as to quickly determine the status of use and the aging characteristics of the composite material. In the present invention, the inspection of an aging state of a silicone rubber composite material is accomplished by taking advantages of the characteristic that the characteristic spectral line is sensitive to the state of a specimen to be tested. Compared with the inspection method and instrument used in the prior art, the method of the present invention has the advantages of no need of particular sampling, convenient operation, and fast analysis (where the whole analysis process spends no more than 30 s), and can be used to analyze and determine the aging state of multiple sheds of multiple insulator strings and a single insulator on a tower during the interruption maintenance process. By adopting the present invention, the aging state of a composite material of a power transmission line can be quickly determined, and then replacement or maintenance is made according to practical situations, to ensure the safe operation of a power system.

BRIEF DESCRIPTION OF THE DRAWINGS

The present invention will become more fully understood from the detailed description given herein below for illustration only, and thus are not limitative of the present invention, and wherein.

DETAILED DESCRIPTION

Figure 1:
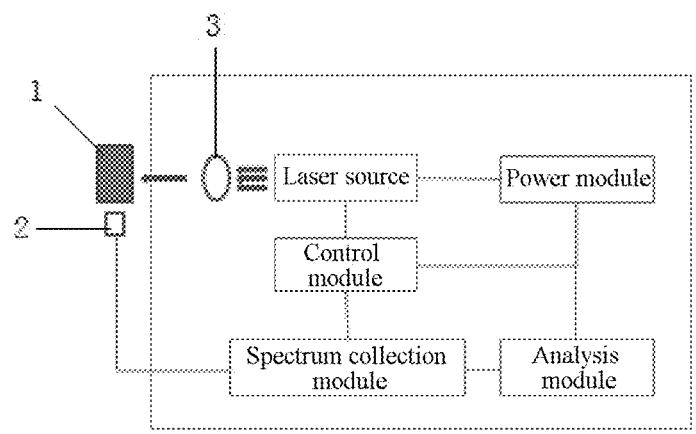
FIG. 1 shows the principle of an LIBS system used in an embodiment of the present invention.

The present disclosure is described in further detail below with reference to embodiments and the accompanying drawings.

The embodiments of the present invention are described in detail below. It is to be emphasized that the following description is merely exemplary and not intended to limit the scope of the present invention and its application.

In an embodiment, a method for inspecting an aging state of a silicone rubber composite insulating material comprises the following steps:

Step S1: bombarding, for multiple times and by a pulsed laser beam, selected points on a surface of a silicone rubber composite insulating material to be inspected to generate a plasma, and measuring a bombardment depth formed in the silicone rubber composite insulating material after each bombardment;

Step S2: collecting spectrum information emitted by the plasma at each bombardment, and extracting, from the collected spectrum information, a spectral property indicator of a specific constituent element of the silicone rubber composite insulating material at each bombardment, wherein the spectral property indicator comprises at least a spectral-line intensity characteristic of a characteristic spectral line;

Step S3: determining a change pattern of the spectral property indicator of the specific constituent element with respect to the bombardment depth; and Step S4: determining aging state information of the silicone rubber composite insulating material according to the change pattern of the spectral property indicator of the specific constituent element with respect to the bombardment depth, wherein the aging state information comprises at least aging depth information of the silicone rubber composite insulating material.

In some embodiments, the silicone rubber composite insulating material is a composite material for power transmission lines and transformer equipment. By means of the present method, an aging state of a composite material for power transmission lines and transformer equipment is inspected. The composite material for power transmission lines may include, but is not limited to, a variety of externally insulating composite materials, for example, an RTV coating of an insulator, a shed material of a composite insulator, or a transformer sheathing material.

In a preferred embodiment, the selected points comprise a plurality of selected points at different locations on the surface of the silicone rubber composite insulating material; and in Step S4, average aging state information of the silicone rubber composite insulating material at the plurality of selected points is determined, so as to determine an aging state of the silicone rubber composite insulating material.

In a preferred embodiment, in Step S1, the selected points on the surface of the silicone rubber composite insulating material to be inspected are bombarded for multiple times by a pulsed laser beam under the same bombardment conditions. In Step S3, a change pattern of the spectral property indicator of the specific constituent element with respect to the number of bombardments is determined, to reflect the change pattern of the spectral property indicator of the specific constituent element with respect to the bombardment depth. In Step S4, the aging depth information of the silicone rubber composite insulating material is determined according to a linear relationship between the bombardment depth and the number of bombardments under the same bombardment conditions and the change pattern of the spectral property indicator of the specific constituent element with respect to the number of bombardments.

Further preferably, the bombardment conditions comprise single pulse energy, frequency, spot area, and angle of bombardment of the pulsed laser beam.

In a preferred embodiment, in Step S2, the specific constituent element detected comprises a first element and a second element, characteristic spectral lines of the first element and the second element at each bombardment are determined from the collected spectrum information, and a spectral line intensity ratio of the second element to the first element is calculated. In Step S3, a change pattern of the spectral line intensity ratio of the second element to the first element with respect to the bombardment depth is determined. In Step S4, the aging state information of the silicone rubber composite insulating material is determined according to the change pattern of the spectral line intensity ratio of the second element to the first element with respect to the bombardment depth.

In a further preferred embodiment, in Step S2, an element with a relatively stable spectral line intensity at the multiple bombardments is selected as the first element, for example, the element Si, and an element with a relatively unstable spectral line intensity at the multiple bombardments is selected as the second element, for example, the element Mg.

In some embodiments, the spectral property indicator for determining the aging state further comprises the temperature and the electron density of the plasma, and so on.

In a further embodiment, the inspection and analysis in above embodiments can be implemented with an LIBS system. As shown in FIG. 1, the LIBS system may include a laser source, a power module, a control module, a spectrum collection module, an analysis module, an optical fiber probe 2, an optical lens 3 and other components, by which the inspection and analysis of a silicone rubber composite insulating material 1 to be inspected is accomplished According to the method provided in the above embodiments, the laser from a pulsed laser source is focused on the surface of an RTV silicone rubber coating of an insulator or the surface of a composite insulator to be inspected, and partially vaporizes the surface of the to-be-inspected silicone rubber composite material to form a plasma. The spectrum information emitted during the plasma expansion and cooling process is collected. The composition of the silicone rubber composite material, the characteristic spectral line intensity of a specific constituent element, the spectral line intensity ratio, the temperature and the electron density of the plasma and other spectral property indicators are extracted from the collected emission spectrum of the plasma. The aging state of the silicone rubber composite material can be determined quickly by making use of the correlation between these indicators and the aging state of the silicone rubber composite material.

According to the above method, in the present invention, on the basis of macro inspection, an LIBS device is employed to inspect the silicon rubber composite material to be tested (RTV coating or a shed material of a composite insulator) by making use of the characteristics that the laser-induced plasma spectrum is extremely sensitive to the characteristic change of an object to be tested and has high spatial resolution, so as to quickly determine the status of use and the aging characteristics of the composite material. In the present invention, the inspection of an aging state of a silicone rubber composite material is accomplished by taking advantages of the characteristic that the characteristic spectral line is sensitive to the state of a specimen to be tested. Compared with the inspection method and instrument used in the prior art, the method of the present invention has the advantages of no need of particular sampling, convenient operation, and fast analysis (where the whole analysis process spends no more than 30 s), and can be used to analyze and determine the aging state of multiple sheds of multiple insulator strings and a single insulator on a tower during the interruption maintenance process. By adopting the present invention, the aging state of a silicone rubber composite material of a power transmission line can be quickly determined, and then replacement or maintenance is made according to practical situations, to ensure the safe operation of a power system.

A method for inspecting an aging state of a silicone rubber composite insulating material according to an embodiment specifically comprises the following operation steps.

(1) m points (where m is preferably greater than 5) are selected in a region of the silicone rubber composite material (an RTV coating of an insulator or a shed of a composite insulator) to be inspected on-site, and each of the selected points is bombarded for Xi times (i=1, 2 . . . m, in which the point is not broken down with the number of bombardments) by a pulsed laser with a particular single pulse energy, frequency, and spot area, at the same angle of bombardment. The depth di (i=1, 2 . . . m) of a laser ablated pit at each point is measured by using a white light interferometer. The results show that there is a linear relationship between the depth di of the laser ablated pit formed in the material and the number Xi of bombardments under the conditions that the single pulse energy, the frequency, the spot area and the angle of bombardment of the laser are constant. The thickness h of the material ablated by each laser bombardment can be obtained from the linear relationship, and different numbers of bombardments correspond to different depths in the material, and the n-th bombardment corresponds to the depth n*h.

(2) n points (where n is preferably greater than 20) are randomly selected in a region of the silicone rubber composite material (an RTV coating of an insulator or a shed of a composite insulator) to be inspected on-site, and each of the selected points is bombarded by a pulsed laser with a particular single pulse energy, frequency, and spot area at the same angle of bombardment by focusing the laser beam on the surface of the composite material to be detected. The plasma spectrum of each point at each bombardment is collected by a spectrum detection module in an LIBS system.

(3) A characteristic spectral line A1 of an element A having a strong and stable spectral intensity in the collected plasma spectra at different numbers of bombardments is selected as a standard spectral line. In a plasma spectrum obtained at a n-th bombardment, a characteristic spectral line B1 of an element B has a spectral line intensity of $I_{B,n}$, and the standard spectral line A1 has a spectral line intensity of $I_{A,n}$, then the intensity ratio of the two spectral lines at this bombardment is $$I_{B/A} = \frac{I_{B,n}}{I_{A,n}}$$

From the above equation, the ratio $I_{B/A}$ of the spectral intensities of the characteristic spectral line B1 to the standard spectral line A1 in the plasma spectrum obtained at each point at each bombardment can be obtained. According to this step, the spectral intensity ratio of the characteristic spectral lines of other elements to the standard spectral line A1 in the plasma spectrum obtained at each point at each bombardment can be obtained (4) A change pattern at each point of the intensity ratio of each characteristic spectral line to the standard spectral line with respect to the number of bombardments can be obtained from Step (3), because a linear relationship exists between the number of bombardments and the depth, and the depth created by each bombardment has already been obtained from Step (1). According to the change pattern of the spectral line intensity ratio, the change of some specific elements in the material at each point with the bombardment depth can be obtained. In general, the composition of the material may fluctuate in space due to the processing process and the like, but the fluctuation is within a certain range without dramatic changes. The change in spectral intensity obtained by this method is attributed to the aging of the silicone rubber composite insulating material, so the curve (see the example shown in FIG. 2) will have a greater change. This change reflects the aging state of the silicone rubber composite material at each point. That is, because of the aging factor, the chemical composition of the silicone rubber composite insulating material varies in the depth direction of the material. According to the pattern, the depth of aging of the silicone rubber composite insulating material and the change of the material composition during the aging process can be obtained, thereby reflecting the aging state of the silicone rubber composite insulating material at these points. The aging state information at 20 points is averaged, to determine the overall aging state of the silicone rubber composite insulating material.

Application Example

Figure 2:
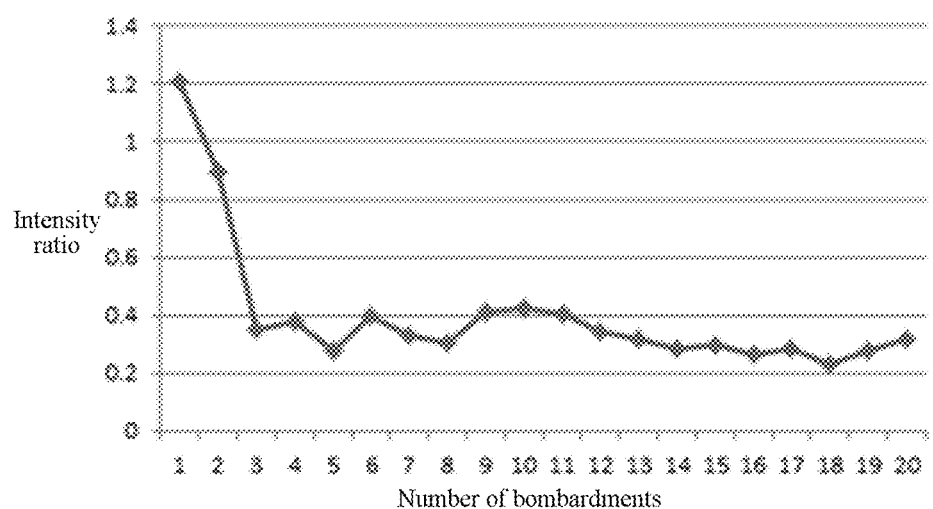
FIG. 2 shows a change pattern of a characteristic spectral line intensity ratio of the element Mg to the element Si with respect to the number of bombardments in an embodiment of the present invention.

Following the above operation steps, an aged silicone rubber shed of a composite insulator was inspected. FIG. 2 shows a change pattern of an intensity ratio of a characteristic spectral line of the element Mg at 279.533 nm to a characteristic spectral line as a standard spectral line of the element Si at 288.095 nm with respect to the number of bombardments. As can be seen from FIG. 2, when the number of bombardments is more than 3, the intensity ratio changes slowly with the number of bombardments, that is, the content of the Mg element is relatively stable deeply inside the shed; and when the number of bombardments is less than 3, the intensity ratio changes remarkably with the number of bombardments, reflecting that the content of the Mg element changes sharply and aging occurs near the surface of shed. The bombardment depth corresponding to 3 times of bombardments is the aging depth of the shed.

Although the present disclosure is described above in further detail through specific embodiments, the present invention is not limited to the specific embodiments. It should be understood by persons of ordinary skill in the art that any simple deduction or replacement made without departing from the spirit of the present invention shall fall within the protection scope of the present invention.

What is claimed is:

1. A method for inspecting an aging state of a silicone rubber composite insulating material, comprising the following steps:
    S1: bombarding, for multiple times and by a pulsed laser beam, selected points on a surface of a silicone rubber composite insulating material to be inspected to generate a plasma, and measuring a bombardment depth formed in the silicone rubber composite insulating material after each bombardment;
    S2: collecting spectrum information emitted by the plasma at each bombardment, and extracting, from the collected spectrum information, a spectral property indicator of a specific constituent element of the silicone rubber composite insulating material at each bombardment, wherein the spectral property indicator comprises at least a spectral-line intensity characteristic of a characteristic spectral line;
    S3: determining a change pattern of the spectral property indicator of the specific constituent element with respect to the bombardment depth; and
    S4: determining changes of chemical compositions of the silicon rubber composite insulating material in along a depth direction of the silicon rubber composite insulating material in accordance with the change pattern, so as to obtain aging depth information of the silicone rubber composite insulating material,
    wherein in Step S1, the selected points on the surface of the silicone rubber composite insulating material to be inspected are bombarded for multiple times by a pulsed laser beam under the same bombardment conditions; in Step S3, a change pattern of the spectral property indicator of the specific constituent element with respect to the number of bombardments is determined, to reflect the change pattern of the spectral property indicator of the specific constituent element with respect to the bombardment depth; and in Step S4, the aging depth information of the silicone rubber composite insulating material is determined according to a linear relationship between the bombardment depth and the number of bombardments under the same bombardment conditions and the change pattern of the spectral property indicator of the specific constituent element with respect to the number of bombardments.

2. The method for inspecting an aging state of a silicone rubber composite insulating material according to claim 1, wherein the selected points comprise a plurality of selected points at different locations on the surface of the silicone rubber composite insulating material; and in Step S4, average aging state information of the silicone rubber composite insulating material at the plurality of selected points is determined.

3. The method for inspecting an aging state of a silicone rubber composite insulating material according to claim 1, wherein the bombardment conditions comprise single pulse energy, frequency, spot area, and angle of bombardment of the pulsed laser beam.

4. The method for inspecting an aging state of a silicone rubber composite insulating material according to claim 1, wherein in Step S2, the specific constituent element detected comprises a first element and a second element, characteristic spectral lines of the first element and the second element at each bombardment are determined from the collected spectrum information, and a spectral line intensity ratio of the second element to the first element is calculated; in Step S3, a change pattern of the spectral line intensity ratio of the second element to the first element with respect to the bombardment depth is determined; and in Step S4, the aging state information of the silicone rubber composite insulating material is determined according to the change pattern of the spectral line intensity ratio of the second element to the first element with respect to the bombardment depth.

5. The method for inspecting an aging state of a silicone rubber composite insulating material according to claim 2, wherein in Step S2, the specific constituent element detected comprises a first element and a second element, characteristic spectral lines of the first element and the second element at each bombardment are determined from the collected spectrum information, and a spectral line intensity ratio of the second element to the first element is calculated; in Step S3, a change pattern of the spectral line intensity ratio of the second element to the first element with respect to the bombardment depth is determined; and in Step S4, the aging state information of the silicone rubber composite insulating material is determined according to the change pattern of the spectral line intensity ratio of the second element to the first element with respect to the bombardment depth.

6. The method for inspecting an aging state of a silicone rubber composite insulating material according to claim 4, wherein in Step S2, an element with a relatively stable spectral line intensity at multiple bombardments is selected as the first element, and an element with a relatively unstable spectral line intensity at multiple bombardments is selected as the second element.

7. The method for inspecting an aging state of a silicone rubber composite insulating material according to claim 4, wherein the spectral property indicator further comprises the temperature and the electron density of the plasma.

8. The method for inspecting an aging state of a silicone rubber composite insulating material according to claim 1, wherein the silicone rubber composite insulating material is a composite material for power transmission lines and transformer equipment.

9. The method for inspecting an aging state of a silicone rubber composite insulating material according to claim 8, wherein the composite material for power transmission lines and transformer equipment is an RTV coating of glass and ceramic insulators, a shed material of composite insulators, or a cannula sheathing material.

10. The method for inspecting an aging state of a silicone rubber composite insulating material according to claim 1, wherein the inspection is carried out with a laser induced breakdown spectroscopy (LIBS) system.

\* \* \* \* \*